(12) United States Patent
Decaudin et al.

(10) Patent No.: US 9,943,520 B2
(45) Date of Patent: Apr. 17, 2018

(54) ORAL FORMULATION AND SUSPENSION OF AN ONCOLOGY DRUG

(71) Applicant: SUN PHARMA GLOBAL FZE, Sharjah (AE)

(72) Inventors: Celine Decaudin, Rosenau (FR); Vincent Rogue, Bouxwiller (FR)

(73) Assignee: SUN PHARMA GLOBAL FZE (AE)

( * ) Notice: Subject to any disclaimer, the term of this patent is extended or adjusted under 35 U.S.C. 154(b) by 0 days.

(21) Appl. No.: 14/769,110

(22) PCT Filed: Feb. 21, 2014

(86) PCT No.: PCT/IB2014/059161
§ 371 (c)(1),
(2) Date: Aug. 20, 2015

(87) PCT Pub. No.: WO2014/128661
PCT Pub. Date: Aug. 28, 2014

(65) Prior Publication Data
US 2016/0008369 A1 Jan. 14, 2016

Related U.S. Application Data

(60) Provisional application No. 61/768,803, filed on Feb. 25, 2013.

(51) Int. Cl.
| | | |
|---|---|---|
| A61K 31/5377 | (2006.01) |
| A61K 47/14 | (2017.01) |
| A61K 9/00 | (2006.01) |
| A61K 9/10 | (2006.01) |
| A61K 47/02 | (2006.01) |
| A61K 47/12 | (2006.01) |
| A61K 47/26 | (2006.01) |
| A61K 47/38 | (2006.01) |
| B65D 81/32 | (2006.01) |

(52) U.S. Cl.
CPC ........ *A61K 31/5377* (2013.01); *A61K 9/0095* (2013.01); *A61K 9/10* (2013.01); *A61K 47/02* (2013.01); *A61K 47/12* (2013.01); *A61K 47/14* (2013.01); *A61K 47/26* (2013.01); *A61K 47/38* (2013.01); *B65D 81/32* (2013.01)

(58) Field of Classification Search
CPC .................................................. A61K 31/5377
See application file for complete search history.

(56) References Cited

U.S. PATENT DOCUMENTS

| 4,680,312 A * | 7/1987 | Johnson ............... A61K 31/557 |
| | | 514/573 |
| 2012/0122866 A1 | 5/2012 | Fritze et al. |
| 2012/0208794 A1* | 8/2012 | Sasaki ................. C07D 471/04 |
| | | 514/212.08 |

FOREIGN PATENT DOCUMENTS

WO     2010/033481 A1    3/2010

* cited by examiner

*Primary Examiner* — Zohreh A Fay
(74) *Attorney, Agent, or Firm* — Burns & Levinson LLP; Shawn P. Foley

(57) ABSTRACT

Dry powder formulations for inhalation and their use in the treatment diseases and conditions. The formulation contains a uniform blend of a first spray-dried powder and a second spray-dried powder. The first spray-dried powder contains spray-dried particles of a therapeutically active ingredient dispersed in a pharmaceutically acceptable hydrophobic excipient. The second spray-dried powder contains spray-dried particles formed from a pharmaceutically acceptable hydrophobic excipient but are substantially free of any therapeutically active ingredient. The active ingredient in the first spray-dried powder is loaded sufficiently high to compensate for the second spray-dried powder being substantially free of any active ingredient. A process for preparing such formulations is also described.

6 Claims, No Drawings

ORAL FORMULATION AND SUSPENSION OF AN ONCOLOGY DRUG

BACKGROUND OF THE INVENTION

Drugs are formulated as suspensions for different reasons, but the most common one is poor drug solubility. Suspensions may also be used to mask the poor taste resulting from the dissolved drug in solution. A suspension, however, unlike syrup in which the drug is fully dissolved, requires adequate shaking of the container to re-suspend the drug uniformly before dosing. Difficult re-dispersion of the drug from a sediment, or in the worst case, from caking, will result in under- and overdosing. This problem of variable dosing is also encountered when the patient or the caregiver forgets to shake the container before dosing. It is therefore desirable to produce a suspension that is able to maintain its homogeneity on prolonged storage without shaking.

Sonidegib is also known by its chemical name 2-methyl-4'-trifluoromethoxy-biphenyl-3-carboxylic acid [6-(cis-2,6-dimethyl-morpholin-4-yl)-pyridin-3-yl]amide or N-[6-(cis-2,6-dimethylmorpholin-4-yl)pyridine-3-yl]-2-methyl-4'-(trifluoromethoxy)[1,1'-biphenyl]-3-carboxamide.

Sonidegib is a potent, selective, brain penetrating, and orally bioavailable Smoothend (Smo) antagonist and that positively regulates the Hedgehog (Hh) signal transduction pathway. Sonidegib passes through the blood/brain barrier and can thus be developed for Hh dependent brain tumors, such as medulloblastoma, a brain tumor predominantly seen in children.

BRIEF SUMMARY OF THE INVENTION

The present invention relates to an oral suspension formulation of sonidegib as well as a pharmaceutical kit for the oral suspension itself. It also relates to processes for preparing such compositions. It further relates to method use of the oral suspension. Sonidegib has been challenging to formulate due to poor water solubility and wettability. The formulation provided herein overcomes these challenges.

The pharmaceutical kit is provided, comprising a first container and a second container, wherein the first container further comprises in dry form sonidegib, a filler, a glident and a lubricant, and the second container further comprises an oil. A suspension can be prepared by dispersing sonidegib in powder form into predefined volume of reconstitution media (oil) for single use or in a bottle for multi-use. The patient individual dose will be applied by using a dosing syringe. The suspension in the syringe can be directly given into the child's mouth.

DETAILED DESCRIPTION OF THE INVENTION

The present invention relates to pharmaceutical compositions comprising sonidegib, a filler, a glident, and a lubricant. The formulation provided herein overcomes poor solubility and wettability issues. The pharmaceutical compositions are useful for treating a variety of different diseases, including Hedgehog dependent brain tumors, such as medulloblastoma. The structure of sonidegib is shown below:

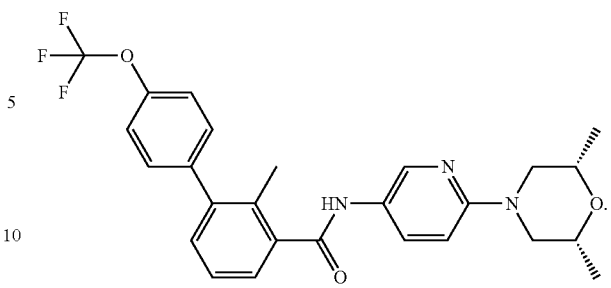

As used herein, "sonidegib" refers to this compound in its free base form, or as a pharmaceutical acceptable salt. An example of a pharmaceutically acceptable salt form of sonidegib is a phosphate salt, which can include monophosphate and diphosphate.

In one aspect of the invention, a pharmaceutical composition is disclosed, comprising sonidegib, or a pharmaceutically acceptable salt thereof, a filler, a glident, a lubricant, and an oil. In another aspect of the invention, provided herein is a pharmaceutical composition comprising sonidegib, microcrystalline cellulose, colloidal silicon dioxide, magnesium stearate, and Miglyol 812.

According to another aspect, the pharmaceutical composition comprises about 30 weight percent sonidegib, about 68 weight percent microcrystalline cellulose, about 0.5 weight percent colloidal silicon dioxide, and about 0.5 weight percent magnesium stearate, relative to the total weight of the sonidegib, microcrystalline cellulose, colloidal silicon dioxide, and magnesium stearate, and Miglyol 812.

In still another aspect, provided herein is a pharmaceutical kit, and is comprised of a first container, further comprising a mixture of sonidegib, a filler, a glident, and a lubricant; a second container further comprising an oil; and a dispensing syringe, a dosing syringe, or both.

In one embodiment, the present invention relates to a pediatric dosage form that is a powder for oral suspension by reconstitution in an oily vehicle. The powder may be comprised of sonidegib in powder form. Alternatively, the powder may be a composition of compounds, including sonidegib in powder form, plus a filler, a glident, and/or a lubricant. The use of an oily vehicle allows manufacturing a dosage form suitable for patient dose flexibility and a higher bioavailability than the current capsule form (outcomes of relative PK study in healthy volunteers).

Poor solubility and wettability issues were improved with the use of an oily vehicle. A preferred oily vehicle is one based on medium-chain triglycerides (MCTs), which are medium-chain (6 to 12 carbons) fatty acid esters of glycerol. An example of a MCT is MIGLYOL, made from various distillation fractions of coconut oil. Miglyol 812, for example, is a medium chain fatty acid triglyceride. MIGLYOL 812 is composed of 55% triglycerides of C8 and 45% triglycerides of C10 fatty acids. MIGLYOL neutral oils are clear, slightly yellowish esters of saturated coconut and palm kernel oil-derived caprylic and capric fatty acids. This oil is clear, virtually colorless liquid of neutral odor and taste.

Other rich sources of MCTs include palm kernel oil and camphor tree drupes. The fatty acids found in MCTs are called medium-chain fatty acids. The names of the medium-chain fatty acids (and the corresponding number of carbons) found in MCTs are caproic acid (C6), caprylic acid (C8), capric acid (C10) and lauric acid (C12). Like all triglycerides (fats and oils), MCTs are composed of a glycerol backbone and three fatty acids, hence the name triglyceride;

in the case of MCTs, 2 or 3 of the fatty acid chains attached to glycerol are medium chain in length. Approximate ratios of these fatty acids in commercial MCT products derived from coconut oil are 2(C6):55(C8):42(C10):1(C12).

The powder and the oily vehicle (e.g., Miglyol 812) may be stored together in a single container. Alternatively, the powder (i.e. sonidegib in powder form or a composition of compounds, including sonidegib in powder form, plus a filler, a glident, and/or a lubricant) may be stored in a separate container from the oily vehicle to ensure that the correct amount of pharmaceutical composition is being provided to the patient at each dose. In one aspect of the invention, a pharmaceutical kit is provided, comprising a first container, further comprising a mixture of sonidegib, a filler, a glident, and a lubricant; a second container further comprising an oil; and a dispensing syringe, a dosing syringe, or both. In an embodiment, the dispensing syringe or dosing syringe is used to transfer a predetermined amount of the sonidegib mixture from the first container to the second container to form a suspension. The suspension can be prepared by dispersing sonidegib in powder form into a predefined volume of reconstitution media (oil) for single use or in a bottle for multi-use. The patient individual dose will be applied by using the dosing syringe. The suspension in the syringe can be directly given into a child's mouth.

According to one embodiment, the oil is a medium chain triglyceride. In one embodiment, the medium chain triglyceride is derived from coconut oil. In another embodiment, the medium chain triglyceride is a Miglyol. In still another embodiment, the Miglyol is selected from the group consisting of Miglyol 808, Miglyol 810, Miglyol 812, Miglyol 818, Miglyol 829, Miglyol 840, Miglyol 8108, and Miglyol 8810. According to an embodiment, the medium chain triglyceride is Miglyol 812.

In an embodiment of the invention, the filler is selected from the group consisting of lactose, dibasic calcium phosphate, saccharide, microcrystalline cellulose, sucrose, dextrose, starch, manitol, and sorbitol, or a mixture thereof. In another embodiment, the filler is microcrystalline cellulose.

In another embodiment, the glident is selected from the group consisting of fumed silicon dioxide, sodium aluminosilicate, calcium silicate, powdered cellulose, colloidal silicon dioxide, microcrystalline cellulose, corn starch, sodium benzoate, calcium carbonate, magnesium carbonate, talc, metallic stearates, calcium stearate, magnesium stearate, zinc stearate, magnesium lauryl sulfate, and magnesium oxide, or a mixture thereof. In still another embodiment, the glident is colloidal silicon dioxide.

According to one embodiment, the lubricant is selected from the group consisting of magnesium stearate, colloidal silicon dioxide, talc, calcium stearate, stearic acid, PEG, glyceryl monostearate, potassium benzoate, sodium stearyl fumarate, glyceryl behenate, mineral oil, or a mixture thereof. According to another embodiment, the lubricant is magnesium stearate.

According to one embodiment of the invention, the weight ratio of sonidegib to the filler is within the range of 1:1.4-2.8, the weight ratio of sonidegib to the glident is within the range of 1:0.007-0.025, and the weight ratio of sonidegib to the lubricant is within the range of 1:0.021-0.043.

According to another embodiment of the invention, the weight ratio of sonidegib to the filler is about 1:2.23, the weight ratio of sonidegib to the glident is about 1:0.0167, and the weight ratio of sonidegib to the lubricant is about 1:0.03.

In yet another embodiment, the weight percentages of the sonidegib, the filler, the glident, and the lubricant are within the range of 25-35%, 55-75%, 0.3-0.7%, and 0.5-1.5%, respectively, relative to the total weight of sonidegib, the filler, the glident, and the lubricant.

In still another embodiment, the weight percentages of the sonidegib, the filler, the glident, and the lubricant are approximately 30 percent, approximately 68 percent, approximately 0.5 percent, and approximately 1 percent, respectively, relative to the total weight of sonidegib, the filler, the glident, and the lubricant.

The ratio of sonidegib to the filler may vary. In one embodiment, the ratio of sonidegib to the filler is about 1:1, by weight. In another embodiment, the ratio of sonidegib to the filler is about 1:1.5, by weight. In still another embodiment, the ratio of sonidegib to the filler is about 1:2, by weight. In still another embodiment, the ratio of sonidegib to the filler is about 1:2.5 by weight. In yet another embodiment, the ratio of sonidegib to the filler is about 1:2.8 by weight. In a further embodiment, the ratio of sonidegib to the filler is 1:3 by weight.

The ratio of sonidegib to the glident may also vary. In one embodiment, the ratio of sonidegib to the glident is about 1:0.007, by weight. In yet another embodiment, the ratio of sonidegib to the glident is about 1:0.008, by weight. In a further embodiment, the ratio of sonidegib to the glident is about 1:0.009, by weight. According to another embodiment, the ratio of sonidegib to the glident is about 1:0.01, by weight. According to yet another embodiment, the ratio of sonidegib to the glident is about 1:0.0167, by weight. In still another embodiment, the ratio of sonidegib to the glident is about 1.0.02, by weight. According to another embodiment, the ratio of sonidegib to the glident is about 1:0.03, by weight.

The ratio of sonidegib to the lubricant may vary. In an embodiment, the ratio of sonidegib to the lubricant is 1:0.02, by weight. In another embodiment, the ratio of sonidegib to the lubricant is about 1:0.03, by weight. In a further embodiment, the ratio of sonidegib to the lubricant is about 1:0.04, by weight. In still another embodiment, the ratio of sonidegib to the lubricant is about 1:0.043, by weight. According to another embodiment, the ratio of sonidegib to the lubricant is about 1:0.05, by weight.

Additionally, the amount of the oily vehicle may vary depending upon the amount of the powder prescribed per dose such that a suspension is formed. In one embodiment, the oil is about 80 mL. In another embodiment, the oil is about 50 mL-about 100 mL. In other embodiments, the volume of oil may be about 7 mL, 10 mL, 15 mL, 20 mL, 25 mL, 30 mL, 35 mL, 40 mL, 45 mL, 50 mL, 55 mL, 60 mL, 65 mL, 70 mL, 75 mL, 80 mL, 85 mL, 90 mL, 85 mL, 100 mL or more, or any derivative therein. The oily vehicle may be stored in a container separate from the powder. When it is time for the medication to be administered to the patient, the correct amount of powder may be mixed with the correct volume of oily vehicle to create a suspension. Alternatively, the oily vehicle may be stored in a container together with the powder, such that the medication is ready for administration.

Therefore, these constitute a preferred dosage form for administration to patients who have difficulty in swallowing solid oral dosage forms like tablets and capsules, especially pediatric population which is the mean part of the medulloblastoma patients. Tutti Frutti flavor and sucralose are both in the formulation to improve the patient compliance. These two compounds improve also the palatability of the suspension as this is an 100% oily suspension. The vehicle, Miglyol 812, has no specific odor or taste.

Accordingly, in one embodiment, the pharmaceutical composition disclosed herein further comprises a flavor or sweetener. Suitable flavoring agents may include those known to the skilled artisan, such as natural, "natural-like" and artificial flavors. These flavors may be chosen, e.g., from synthetic flavor oils, flavoring aromatics, oleo-resins and extracts derived e.g. from plants, leaves, flowers or fruits. Representative flavors may include one or more of spearmint oil, cinnamon oil, peppermint oil, clove oil, bay oil, thyme oil, cedar leaf oil, oil of nutmeg, oil of sage, oil of bitter almonds, vanilla, chocolate, coffee, cocoa and citrus oil, lemon, orange, cherry, grape, lime or grapefruit, and fruit essences, e.g. apple, pear, peach, strawberry, raspberry, cherry, plum, pineapple or apricot; mints such as peppermint (including menthol, especially levomenthol), aldehydes and esters, e.g. cinnamyl acetate, cinnamaldehyde, citral, diethylacetal, dihydrocarvyl acetate, eugenyl formate or p-methylanisol; alpha-citral (geranial) and beta-citral (neral); decanal; ethyl vanillin; piperonal (heliotropine); vanillin; alpha-amyl cinnamaldehyde; butyraldehyde; valeraldehyde; citronellal; decanal; aldehyde C-8; aldehyde C-9; aldehyde C-12; 2-ethyl butyraldehyde; hexenal, i.e. trans-2; tolyl aldehyde; veratraldehyde; 2,6-dimethyl-5-heptenal (melonal); or 2-6-dimethyloctanal; 2-dodecenal.

According to one aspect of the invention, the pharmaceutical composition comprises sonidegib phosphate, microcrystalline cellulose, Tutti Frutti flavor, magnesium stearate, sucralose, colloidal silicon dioxide. The invention can be free of preservatives.

In one embodiment of the invention, the pharmaceutical composition comprises about 1410 mg sonidegib phosphate, about 2149 mg microcrystalline cellulose, about 47 mg Tutti Frutti flavor, about 47 mg magnesium stearate, about 23.5 mg sucralose, about 23.5 mg colloidal silicon dioxide, and 50-100 mL Miglyol 812, wherein the Miglyol 812 may be combined with the pharmaceutical composition, or stored separately from the pharmaceutical composition and mixed with the pharmaceutical composition prior to administration.

According to another embodiment, the pharmaceutical composition comprises about 5206 mg sonidegib phosphate, about 11627 mg microcrystalline cellulose, about 174 mg Tutti Frutti flavor, about 87 mg magnesium stearate, about 87 mg sucralose, about 174 mg colloidal silicon dioxide, and 50-100 mL Miglyol 812, wherein the Miglyol 812 may be combined with the pharmaceutical composition, or stored separately from the pharmaceutical composition and mixed with the pharmaceutical composition prior to administration.

In another aspect of the invention, the pharmaceutical composition comprises sonidegib, microcrystalline cellulose, Tutti Frutti flavor, sucralose, Aerosil 200, magnesium stearate and Miglyol 812. According to one embodiment, the pharmaceutical composition comprises about 300 mg sonidegib, about 670 mg microcrystalline cellulose, about 10 mg Tutti Frutti flavor, about 5 mg sucralose, about 5 mg Aerosil 200, about 10 mg magnesium stearate; and 50-100 mL Miglyol 812, wherein the Miglyol 812 may be combined and stored together with the pharmaceutical composition, or stored separately from the pharmaceutical composition and mixed with the pharmaceutical composition prior to administration.

An example of a pharmaceutical composition of the present invention is sonidegib, microcrystalline cellulose, colloidal silicon dioxide, magnesium stearate, and Miglyol 812.

Methods of Treatment

Sonidegib has been shown to inhibit the hedgehog signaling pathway and can potentially treat cancer and proliferative diseases that include, but are not limited to solid tumors, carcinomas, cancers of the brain, muscle and skin, prostate, glioma, glioblastoma, medulloblastoma and other primary CNS malignant neuroectodermal tumors, digestive tract tumors including pancreatic cancer including adenocarcinomas, breast, basal cell carcinoma small-cell lung carcinomas, hematologic malignancies, leukemias, including ALL, AML, CIVIL, multiple myeloma, myelofibrosis, sarcoma, osteosarcoma, liposarcoma, rhabdomyosarcoma, melanoma. Enhanced activation of the hedgehog signaling pathway contributes to the pathology and/or symptomology of a number of diseases. Accordingly, molecules that modulate the activity of the hedgehog signaling pathway are useful as therapeutic agents in the treatment of such diseases.

In an embodiment, a method of treating medulloblastoma in a patient is disclosed, comprising administering to said patient a therapeutically effective amount of a pharmaceutical composition, or a pharmaceutically acceptable salt thereof. In an embodiment, the patient is between 0 and 19 years of age.

In accordance with the following, the present invention further provides a method for preventing or treating any of the diseases or disorders described above in a subject in need of such treatment, which method comprises administering to said subject a therapeutically effective amount of the pharmaceutical composition provided herein. For any of the above uses, the required dosage will vary depending on the mode of administration, the particular condition to be treated and the effect desired.

In one embodiment, a therapeutically effective amount of the agent is given to a subject using the pharmaceutical compositions provided herein. The term "therapeutically effective" amount is further meant to define an amount resulting in the improvement of any parameters or clinical symptoms. The actual dose may vary with each patient and does not necessarily indicate a total elimination of all disease symptoms.

A therapeutically effective amount of the compositions used in the treatment described herein may be readily determined by the attending diagnostician, as one skilled in the art, by the use of conventional techniques and by observing results obtained under analogous circumstances. In determining the effective dose, a number of factors are considered by the attending diagnostician, including, but not limited to: the species of mammal; its size, age, and general health; the specific disease involved; the degree of or involvement or the severity of the disease; the response of the individual patient; the particular compound or composition administered; the mode of administration; the bioavailability characteristic of the preparation administered; the dose regimen selected; the use of concomitant medication; and other relevant circumstances.

Dosing for Children

The use of a suspension for oral administration to children is preferred as it is convenient and the dosage can be accurately controlled. In combination with an appropriate metering system, e.g. calibrated syringes or pipettes, an oral suspension provides high flexibility in controlling the dosage. This facilitates administration to children of different sizes or at different stage of the disease, with varying dosage requirements. Additionally, an oral suspension allows the use of flavoring and/or palatability agents that can promote patient acceptance and compliance, which can be particularly advantageous when dosing chronically to children.

Therefore, these constitute a preferred dosage form for administration to patients who have difficulty in swallowing solid oral dosage forms like tablets and capsules, especially pediatric population which is the mean part of the medulloblastoma patients. Tutti Frutti flavor and sucralose are both in the formulation to improve the patient compliance. These two compounds improve also the palatability of the suspension as this is an 100% oily suspension. The vehicle, Miglyol 812, has no specific odor or taste.

Concentration of excipients is fixed to allow dose flexibility from 100 mg to approximately 650 mg with 50 mg increments. Patients are dosed on an mg/m2 basis with rounding to the nearest 50 mg dose. Liquid formulation preferred for toddlers and children who may have difficulties swallowing.

A method of treating medulloblastoma in a patient is disclosed, comprising administering to the patient a therapeutically effective amount of the pharmaceutical composition provided herein. In an embodiment, the patient is between 0 and 19 years of age.

"Treat", "treating" and "treatment" refer to a method of alleviating or abating a disease and/or its attendant symptoms. The present invention relates to the discovery that signal transduction pathways regulated by hedgehog, patched (Ptc), gli and/or smoothened can be modulated by the pharmaceutical composition contained here.

EXEMPLIFICATION

The preparation and properties of N-(6-((2R,6S)-2,6-dimethylmorpholino)pyridin-3-yl)-2-methyl-4'-(trifluoromethoxy)-[1,1'-biphenyl]-3-carboxamide (sonidegib, LDE225) are provided in International Patent Application No. PCT/US2007/068292 (referred to therein as "compound 153"), the entire contents of which is incorporated herein by reference.

Dissolution of the oral suspension was shown to be immediate and delivery of poorly soluble drug substance with high specific surface area/poor wettability and high dose (up to 600 mg). The present invention improved bioavailability and reduce the amount of drug product needed to reach the same effect.

Example 1

Solubility of Sonidegib Phosphate in Various Media:

| Solvent | Solubility (mg/mL) |
| --- | --- |
| 0.1N HCl, pH 1.0 | 0.004 |
| 0.01N HCl, pH 2.0 | 0.018 |
| Acetate buffer, pH 4.5 | <0.0002 |
| Phosphate buffer, pH 6.8 | <0.0002 |
| Phosphate buffer, pH 7.4 | <0.0002 |
| Water | 0.007 |

Sonidegib has a very high surface area (270 m2/g) and a porous structure that leads to poor water solubility.

Example 2

Composition:

| | Batch scale for the master: 1 batch = 300 units[1] up to 2000 units i.e. 5206 g up to 34708 g | | |
| --- | --- | --- | --- |
| Component | Composition per unit [mg/g] | Composition per unit [mg/unit] | Quantity per 34000 [g/batch] |
| Sonidegib | 300 | 5206 | 10200 |
| Cellulose MK GR | 670 | 11627 | 22780 |
| Tutti frutti Dry flavor | 10 | 174 | 340 |
| Sucralose | 5 | 87 | 170 |
| Aerosil 200 | 5 | 87 | 170 |
| Magnesium Stearate | 10 | 174 | 340 |
| Total | 1000.0 | 17354 | 34000 |

[1]One unit corresponds to one 125 ml amber glass bottle.
[2]The drug substance quantity can be adjusted if the content is <99.5%. Respective compensation is done by adjusting the Cellulose MK GR content.

Example 3

A contained manufacturing process is used as sonidegib is highly potent. Excipients and sonidegib are separately weighed and transferred to container where they are blended. Composition is screened and then blended again. Composition is then weighed to be placed in bottles. After composition is placed in bottles, individual adaptors are added. Bottles are closed with a cap. Bottles are labeled and placed in aluminum bag, which is then induction sealed and labeled.

Example 4

In a clinical study of relative bioavailability was performed comparing 200 mg capsules with 200 mg tablet and the oral suspension equivalent to 200 mg. Results are shown below in Tables 1 and 2

TABLE 1

Ratio of geometric means & [90% confidence interval] for AUCO-14d

| | 200 mg |
| --- | --- |
| Oral suspension:Capsule | 1.36 [0.90-2.06]; n = 12, 11 |

TABLE 2

Ratio of geometric means & [90% confidence interval] for Cmax

| | 200 mg |
| --- | --- |
| Oral suspension:Capsule | 1.05 [0.69-1.60]; n = 12, 12 |

The oral suspension provided an AUC than was 36% higher than a conventional capsule and lower variability compared to the other available solid dosage forms.

Example 5

Composition of Sonidegib 1410 mg Powder for Oral Suspension:

| Ingredient | Amount per bottle of sonidegib 1410 mg powder for oral suspension [mg] | Function |
|---|---|---|
| Sonidegib phosphate[1] | 1410.00 | Active substance |
| Cellulose, microcrystalline/ Microcrystalline cellulose | 3149.00 | Filler |
| Tutti Frutti flavor, dry | 47.00 | Flavoring Agent |
| Magnesium Stearate | 47.00 | Lubricant |
| Sucralose | 23.50 | Sweetening agent |
| Silica, colloidal anhydrous/ Colloidal silicon dioxide | 23.50 | Glident |
| Total [mg] | 4700.00 | |

[1]1.40 mg of sonidegib phosphate is equivalent to 1.00 mg of sonidegib free form.

Example 6

Composition of Sonidegib 213.7 mg/g Powder for Oral Suspension:

| Ingredient | Amount of sonidegib 213.7 mg/g powder for oral suspension [mg/unit] | Function |
|---|---|---|
| Sonidegib phosphate[1] | 5206 | Active substance |
| Cellulose, microcrystalline/ Microcrystalline cellulose | 11627 | Filler |
| Tutti Frutti flavor, dry | 174 | Flavoring agent |
| Magnesium Stearate | 87 | Lubricant |
| Sucralose | 87 | Sweetening agent |
| Silica, colloidal anhydrous/ Colloidal silicon dioxide | 174 | Glident |
| Total weight [mg] | 17354 | |

[1]1.404 mg of sonidegib phosphate is equivalent to 1.000 mg of sonidegib free base.

What is claimed is:

1. An oral suspension pharmaceutical composition, comprising 200 mg to 300 mg of sonidegib or a pharmaceutically acceptable salt thereof, a filler comprising microcrystalline cellulose, a glident comprising colloidal silicon dioxide, a lubricant comprising magnesium stearate, a flavor or sweetener and an oil wherein the oil comprises a medium chain fatty acid triglyceride comprising 55% triglycerides of C8 fatty acids and 45% triglycerides of C10 fatty acids.

2. The oral suspension pharmaceutical composition of claim 1, wherein the flavor or sweetener is Tutti Frutti or sucralose.

3. The oral suspension pharmaceutical composition of claim 1, wherein the pharmaceutical composition comprises about 30 weight percent of sonidegib or a pharmaceutically acceptable salt thereof, about 68 weight percent of microcrystalline cellulose, about 0.5 weight percent of colloidal silicon dioxide, and about 0.5 weight percent of magnesium stearate, relative to the total weight of the sonidegib or a pharmaceutically acceptable salt thereof.

4. The oral suspension pharmaceutical composition of claim 1, wherein the pharmaceutical composition comprises 300 mg of sonidegib, about 670 mg of microcrystalline cellulose, about 10 mg Tutti Frutti flavor, about 5 mg sucralose, about 5 mg anhydrous colloidal silicon dioxide, and about 10 mg magnesium stearate.

5. The oral suspension pharmaceutical suspension of claim 1, wherein the amount of sonidegib is 200 mg.

6. An oral suspension pharmaceutical composition, comprising 200 mg to 300 mg of sonidegib or a pharmaceutically acceptable salt thereof, a filler comprising microcrystalline cellulose, a glident comprising colloidal silicon dioxide, a lubricant comprising magnesium stearate, a flavor or sweetener and an oil wherein the oil comprises a medium chain fatty acid triglyceride comprising 55% triglycerides of C8 fatty acids, 42% triglycerides of C10 fatty acids, 2% C6 fatty acids and 1% C12 fatty acids.

* * * * *